United States Patent
Revie et al.

(10) Patent No.: US 9,775,626 B2
(45) Date of Patent: Oct. 3, 2017

(54) METHOD OF CUTTING FOR USE IN SURGERY

(75) Inventors: Ian Revie, Boroughbridge (GB); Michal Slomczykowski, Buchrain (CH)

(73) Assignee: DePuy International Limited, Leeds (GB)

(*) Notice: Subject to any disclaimer, the term of this patent is extended or adjusted under 35 U.S.C. 154(b) by 1199 days.

(21) Appl. No.: 12/891,259

(22) Filed: Sep. 27, 2010

(65) Prior Publication Data

US 2011/0082460 A1 Apr. 7, 2011

Related U.S. Application Data

(63) Continuation of application No. 10/505,304, filed as application No. PCT/GB03/00817 on Feb. 26, 2003, now abandoned, application No. 12/891,259, which is a continuation of application No. 10/505,266, filed as
(Continued)

(30) Foreign Application Priority Data

Feb. 27, 2002 (GB) .................................. 0204549.0

(51) Int. Cl.

| A61B 17/16 | (2006.01) |
|---|---|
| A61B 90/96 | (2016.01) |
| A61B 90/00 | (2016.01) |
| A61B 34/20 | (2016.01) |
| A61B 90/10 | (2016.01) |
| A61B 90/90 | (2016.01) |

(52) U.S. Cl.
CPC .......... *A61B 17/1615* (2013.01); *A61B 34/20* (2016.02); *A61B 90/36* (2016.02); *A61B 90/96* (2016.02); *A61B 17/16* (2013.01); *A61B 90/10* (2016.02); *A61B 90/39* (2016.02); *A61B 90/90* (2016.02); *A61B 2034/2065* (2016.02)

(58) Field of Classification Search
CPC . A61B 2034/2065; A61B 34/20; A61B 90/10; A61B 90/36; A61B 90/39; A61B 90/90; A61B 17/16; A61B 17/1615
USPC ...... 606/172, 173, 180, 79, 130; 600/37, 38, 600/39, 45, 159, 166–171
See application file for complete search history.

(56) References Cited

U.S. PATENT DOCUMENTS

| 5,437,280 A | * | 8/1995 | Hussman | ...................... 600/417 |
|---|---|---|---|---|
| 5,797,849 A | | 8/1998 | Vesely et al. | |
| 6,021,343 A | | 2/2000 | Foley et al. | |

(Continued)

FOREIGN PATENT DOCUMENTS

| CH | 664725 A5 | 3/1988 |
|---|---|---|
| WO | 9103982 A1 | 4/1991 |

(Continued)

*Primary Examiner* — Samuel Hanna
(74) *Attorney, Agent, or Firm* — Maginot, Moore & Beck LLP

(57) ABSTRACT

A surgical instrument system includes a tool (2) including an elongate shaft which defines the tool axis. The shaft bears a plurality of marker rings (10, 11, 12) arranged in a predetermined pattern on the surface of the shaft so that they extend around the shaft axis. The system includes at least two receiving devices (14) which are spaced apart for receiving stereoscopic signals from the rings on the tool, and a data processor (16) for analyzing the signal from the rings and generating information relating to the position and orientation of the tool relative to the receiving device.

15 Claims, 1 Drawing Sheet

Related U.S. Application Data application No. PCT/GB03/00822 on Feb. 26, 2003, now abandoned.

(56) References Cited

U.S. PATENT DOCUMENTS

| | | | |
|---|---|---|---|
| 6,203,493 B1* | 3/2001 | Ben-Haim | 600/117 |
| 6,246,898 B1 | 6/2001 | Vesely et al. | |
| 6,272,370 B1* | 8/2001 | Gillies et al. | 600/411 |
| 6,317,616 B1 | 11/2001 | Glossop | |
| 6,332,891 B1 | 12/2001 | Himes | |
| 6,478,802 B2* | 11/2002 | Kienzle et al. | 606/130 |
| 2002/0016599 A1* | 2/2002 | Kienzle et al. | 606/130 |
| 2004/0267268 A1* | 12/2004 | Gillespie et al. | 606/80 |

FOREIGN PATENT DOCUMENTS

| | | |
|---|---|---|
| WO | 0054687 A1 | 9/2000 |
| WO | 0164124 A1 | 9/2001 |

* cited by examiner

METHOD OF CUTTING FOR USE IN SURGERY

This application is a continuation of both (i) co-pending application Ser. No. 10/505,304, filed Jul. 11, 2005 and (ii) co-pending application Ser. No. 10/505,266 filed May 13, 2005. Co-pending application Ser. No. 10/505,304 is a National Stage (under 35 U.S.C. 371) of International Application No. PCT/GB03/00817, filed Feb. 26, 2003. Co-pending application Ser. No. 10/505,266 is a National Stage (under 35 U.S.C. 371) of International Application No. PCT/GB03/00822, filed Feb. 26, 2003. Note that both (i) International Application No. PCT/GB03/00817, and (ii) International Application No. PCT/GB03/00822 claims priority to United Kingdom Patent Application No. GB0204549.0, filed on Feb. 27, 2002. The disclosures of both (i) co-pending application Ser. No. 10/505,304, and (ii) co-pending application Ser. No. 10/505,266 are hereby totally incorporated by reference in their entirety.

The present invention relates to a surgical instrument system. The system finds particular application in the field of image guided surgery.

Some surgical techniques can be automated using computer apparatus. For example, it is known to use computers to generate signals to control the position of surgical instruments. These techniques can be used for example in conjunction with image data relating to the patient, for example as to the location, size, orientation etc of tissue on which the procedure is to be performed. In particular, if the location of the surgical instrument can be determined relative to the tissue on which the procedure is to be performed, it is possible in some circumstances for manipulation of the instrument to be controlled throughout the procedure using signals generated by a computer.

Reliable performance of such automated surgical procedures requires that the position of the instrument should be determined accurately. This can be done using one or more detectors which can detect signals from the instrument. For example, markers can be provided on the instrument from which a signal can be detected. The markers can be passive, for example made from reflective material, or they can be active, for example comprising two or more devices which emit radiation (such as light emitting diodes).

In the case of a surgical tool which is rotated about its axis such as a drill bit, it is known to provide markers for monitoring the position of the drive unit for the tool. This has can give rise to inaccuracies when the tool is long, when the end of the rotating part (whose location is likely to be of greatest significance) is spaced apart from the markers on the drive unit, for example due to flexing of the tool.

The present invention provides a surgical instrument system in which ring markers are placed on the shaft of a tool.

Accordingly, in one aspect, the invention provides a surgical instrument system, which comprises:

a. a tool including an elongate shaft which defines the tool axis, the shaft bearing a plurality of marker rings arranged in a predetermined pattern on the surface of the shaft so that they extend around the shaft axis, b. at least two receiving devices which are spaced apart for receiving stereoscopic signals from the rings on the tool, c. a data processor for analysing the signal from the rings and generating information relating to the position and orientation of the tool relative to the receiving device.

The instrument system of the present invention has the advantage that it enables position signal data to be obtained from a tool without the need for markers to be provided on a handle or other control part. The signal data can therefore be obtained from a part of the instrument which can be close to the end of the tool which is in contact with a patient's tissue; the signal data is therefore not subject to inaccuracies that can be associated with markers located on a handle or drive unit, for example arising from flexing of the tool.

The nature of the marker rings on the shaft of the tool are such that they will appear when viewed by the receiving device as rectangles when the tool is viewed from one side, perpendicular to a plane containing the axis of the tool, especially when the shaft is rotating about its axis. When the device is viewed obliquely from one side, the appearance of the rings will deviate from being exactly rectangular in that the sides of the rectangular will appear curved.

Preferably, the marker rings will extend continuously around the shaft of the tool. However, for some applications, the marker rings can have a small break provided in them, provided that the break does not interfere significantly with determining the location and spacing of the edges of the ring.

Preferably, the planes defined by the axially spaced edges of each ring are parallel to one another and perpendicular to the axis of the shaft. The rings will then appear as rectangles when the tool is viewed from one side perpendicular to a plane containing the axis of the tool. When the tool is viewed obliquely from one side, the edges of the rings will appear curved and will be continuously equidistant (parallel) around the axis of the tool. This has the advantage that it can facilitate analysis of the position data relating to the rings by the computer, even when the edges of the rings do not appear to the receiving device to be straight.

Determining the position of the tool will often require accurate determination of the relative positions of the rings when viewed by the receiving device. Steps which can be included in the determination of their relative positions can include one or more of:

a. locating the axis of the shaft, which will generally extend along a line which is equidistant from the opposite edges (extending parallel to the shaft axis) of the rings, and b. locating the centre line of each ring, which will intersect the axis of the shaft at a point which is equidistant from the opposite edges (extending perpendicular to the shaft axis) of the rings.

Preferably, the data processor is programmed to perform the steps of:

a. locating the axis of the shaft, which will generally extend along a line which is equidistant from the opposite edges (extending parallel to the shaft axis) of the rings, and b. locating the centre line of each ring, which will intersect the axis of the shaft at a point which is equidistant from the opposite edges (extending perpendicular to the shaft axis) of the rings.

Preferably, the data processor is programmed to perform the steps of:

a. identifying three generally rectangular areas which represent the rings on the shaft when the shaft is viewed from one side, b. determining the location of a line on each of the rectangular areas which represents the midpoint of each area, measured parallel to the axis of the tool, c. determining the angle between the lines on adjacent ones of the rectangles.

Especially when the rings are narrow, it might be the relative positions of the rings can be determined with sufficient accuracy without locating their centre lines (step (b) above), thereby reducing the errors in position.

The steps for determining the relative positions of the rings when viewed by the receiving device can be performed by the data processor, for example by determining the coordinates of the relevant edges, and then interpolating to locate the relevant centre line.

Preferably, the system includes at least three marker rings on the surface of the shaft. Preferably, the distance between a first ring and a second ring which is adjacent to the first ring is the same as the distance between the said second ring and a third ring which is adjacent to the second ring on the opposite side of the second ring from the first ring.

The rings on the shaft can be used to provide information about the tool. For example they can be used to identify the tool. This can be achieved by providing the rings in a predetermined arrangement which can be identified by the system. For example, the rings can be provided on the shaft as a bar code as is known from other contexts.

The width of the rings, measured along the axis of the shaft, will be selected according to factors such as the nature of the receiving device and the signals which are received by the device from the rings, and the distance between the tool and the receiving device. The rings should be sufficiently wide that they can be seen by the receiving device. However, it will often be preferred for the width of the rings to be kept to a minimum, consistent with the requirement for visibility, so that inaccuracies in determining the relative positions of the rings are minimised.

Preferably, the width of each ring is less than about 10 mm, for example less than about 5 mm. Generally the width of each ring will be at least about 3 mm.

Preferably, the spacing between adjacent edges of adjacent rings will be at least about 1 mm, more preferably at least about 3 mm, especially at least about 5 mm. Preferably, the spacing is not more than about 20 mm, more preferably not more than about 10 mm.

The rings can have a surface which is a contrasting colour or texture from the remainder of the shaft on which the rings are arranged. For example, the shaft might have a generally dull surface and the rings might have a relatively smooth surface, especially so that it is glossy. The shaft might have a generally dark surface, and the rings might be relatively bright. Accordingly, it is preferred that the marker rings are more reflective than the surface of the shaft on which they are arranged.

The shaft of the tool will generally be made from a metal. Metals which are frequently used in the manufacture of surgical instruments, especially cutting tools, include certain stainless steels. The rings will often be applied using a different material, for example a polymeric material or an inorganic material. The nature of the material of the rings will be selected according to factors such as (a) its reflective or other properties which are necessary for the rings to be detected by the receiving device, and (b) the conditions to which the rings will be exposed prior to, during, and after use of the instrument. When the rings are applied to the shaft of the tool and are intended to remain their permanently, they might be required to withstand the conditions to which the tool is exposed when the tool is prepared for use, for example by exposure to elevated temperature and pressure. Certain pigments (which might be based on polymeric materials) can be suitable. For example, a pigment can be included in a curable polymeric material such as an epoxy resin. Different factors might apply when rings are applied to the shaft of the tool for the purpose of a single procedure. For example, the rings can be provided as markings on a polymeric sleeve, for example provided by an ink. A preferred construction of sleeve might comprise a sleeve formed from a transparent polymeric material, with a plurality of contrasting bands located on the internal surface of the sleeve.

The materials used in the rings will depend on the nature of the receiving device. When the device is a camera which can observe visible radiation, the rings should contrast visibly with the surface of the shaft on which they are arranged. When the device receives data which is not in the visible region of the electromagnetic spectrum, different ring materials might be used. For example, if the device receives infrared or ultraviolet radiation, the rings should reflect radiation from an infrared source or an ultraviolet light source respectively.

The system of the invention includes two (or more) receiving devices which are spaced apart, for receiving stereoscopic signals from the rings on the tool, and possibly three or more receiving devices for accurate determination of the position and, especially, the orientation of a tool. The use of a plurality of appropriately positioned receiving devices allows orientation to be determined by identifying the effect of parallax on the observed spacing between adjacent rings. The use of two receiving devices also allows position and orientation of a tool to be monitored with reduced risk of obstruction of the line of sight.

The positions of the receiving devices will be determined in order to optimise the range of motion of the tool without obstruction of the line of sight of the tool using the devices. Preferably, the general lines of sight for the receiving devices are not parallel to one another so that the angle between the lines of sight is generally less than 150°, for example less than about 120°. The said angle will generally be more than about 30°, for example more than about 60°.

The rings can be provided on the shaft on a sleeve which is applied to the surface of the shaft. For example, the sleeve can be made from a material which allows the sleeve to shrink when subjected to an appropriate treatment such as heating or exposure to a liquid. The rings can instead be provided directly on the surface of the shaft, for example by the application of a layer of contrasting material onto the surface of the shaft, or by engraving the surface of the shaft, or by a combination of the two.

It will generally be necessary to register the tool in the coordinate space defined with respect to the receiving device. The registration process can have the purpose of any of (a) determining the nature of the instrument, and (b) determining the spatial relationship between the rings on the shaft and an operating part (for example the end where cutting teeth are located) of the tool. The nature of the registration process will be different if the rings are applied to the tool on a separate sleeve compared with a tool on which the rings are provided as permanent features. The nature of registration procedures in image guided surgery is generally established.

The tool can be a cutting tool, for example a drill or a reamer. The tool can have other functions, for example as another type of finisher such as a polisher.

Preferably, the system of the invention includes a drive unit for imparting rotational motion to the tool. For example, the drive unit can be of a kind that is used conventionally to impart rotational motion to a tool such as a drill bit. The invention has particular advantages when used in this way, in that the markers are visible on the shaft of the tool throughout its rotation. However, the invention has related advantages when the tool does not rotate about its shaft because the markers can be observed irrespective of the orientation of the tool.

The dimensions of the shaft will vary according to the nature of the tool and its intended application. The shaft will often have a circular cross-section. Its diameter might be less than about 25 mm, for example less than about 20 mm, possibly less than about 10 mm, even less than about 5 mm. The length of the shaft will generally be kept to a minimum, consistent with being able to use the tool at a desired location. However, it will be appreciated that the shaft might be long for some applications, and it is there that the advantages that are afforded by the present invention become particularly significant. Preferably, the rings on the shaft will be positioned as close as reasonably possible to the end of the tool that is remote from the drive unit.

Embodiments of the present invention will now be described by way of example with reference to the accompanying drawings, in which.

Figure 1:
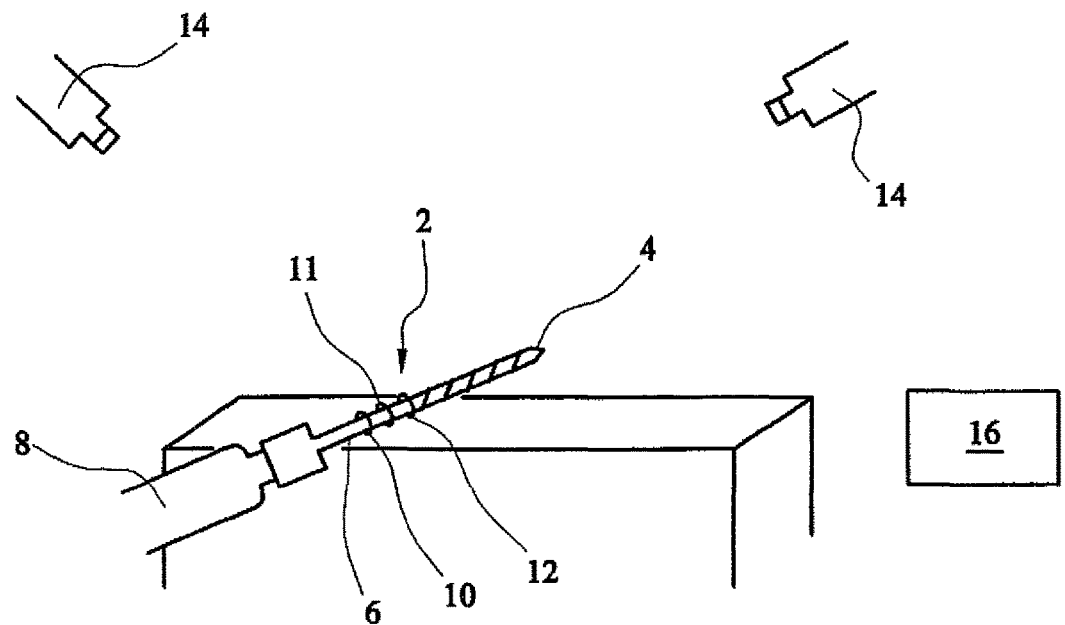
FIG. 1 is a schematic representation of a system according to the present invention.
Figure 2:
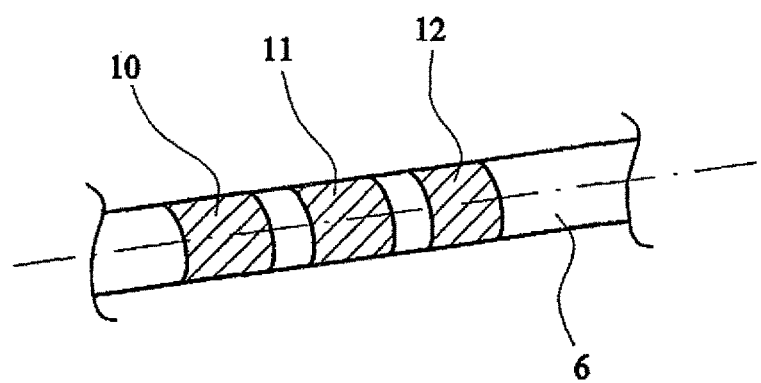
FIG. 2 is a side view of a cutting tool for use in the system of the invention.

Referring to the drawings, FIG. 1 shows a surgical instrument system which comprises a rotatable drill bit 2 having an elongate shaft. The shaft has a cutting portion 4 and a smooth surface portion 6. The drill bit is made from a surgical grade stainless steel. The diameter of the shaft is 6 mm in the illustrated embodiment, although it will be appreciated that the drill bit could have a size which is bigger than this or smaller than this.

The system includes a drive unit 8 which the drill bit 2 fits into, and which causes the drill bit to rotate about the axis defined by the shaft.

The smooth surface portion 6 of the shaft has first, second and third marker rings 10, 11, 12 on its surface. Each of the rings has a width (measured along the axis of the shaft) of 4 mm. The distance between adjacent edges of adjacent rings is 3 mm so that the centre to centre spacing of the rings is 7 mm. The rings on the surface of the shaft are provided by a curable polymeric material such as an epoxy material containing an appropriate pigment.

The system includes two cameras 14, positioned with respect to the drive unit and cutting tool so that the rings on the shaft of the cutting tool are visible throughout use of the cutting tool in a surgical procedure. The pigment should be such that reflected light from the surface of the drill bit enables a sharp contrast to be observed between the rings and the regions of the shaft between the rings.

The system includes a data processor 16 which can analyse the signals received from the cameras. The signals are analysed to determine the spacing between adjacent pairs of the rings, that is between the first and second rings, and between the second and third rings, as viewed by each camera. Determining the spacing involves (a) locating the axis of the shaft, which will generally extend along a line which is equidistant from the opposite edges (extending parallel to the shaft axis) of the rings, and (b) locating the centre line of each ring, which will intersect the axis of the shaft at a point which is equidistant from the opposite edges (extending perpendicular to the shaft axis) of the rings. If the shaft of the tool is arranged so that it extends precisely perpendicular to a line which extends between the camera and the rings, the measured distances between the first and second rings, and between the second and third rings, respectively, will be the same. If the shaft of the tool is arranged so that the shaft is not exactly perpendicular to the line extending between the camera and the rings, the measured distances between the first and second rings, and between the second and third rings, respectively, will be different. For example when the third ring is further from the camera than the first ring, the measured distance between the first and second rings will be greater than the measured distance between the second and third rings. The orientation of the tool relative to the camera (which can be considered in terms of the angle between the shaft axis and the line extending between the camera and the rings) can be determined by simple trigonometry from knowledge of the apparent distances as determined from the receiving device and the actual distances as known from the registration of the tool.

What is claimed is:

1. A method of cutting for use in surgery, which comprises:
   providing a cutting tool comprising an elongate shaft that defines a tool axis and a cutting portion at a first end, the shaft bearing a plurality of marker rings towards a second end of the cutting tool opposite to the first end, the plurality of marker rings arranged in a predetermined pattern on a surface of the shaft and extending at least partially around the tool axis;
   causing the cutting tool to rotate about the tool axis using a drive unit that grips the cutting tool at the second end thereby rotating the plurality of marker rings;
   using at least two spaced apart receiving devices to detect the rotating plurality of marker rings; and
   generating information as to the position and orientation of the cutting portion relative to the receiving devices by analyzing a respective outline of each of the rotating plurality of marker rings as detected by the receiving devices.

2. The method of claim 1, wherein the plurality of marker rings are more reflective than the surface of the shaft on which they are arranged.

3. The method of claim 1, wherein the plurality of marker rings comprises a first marker ring, a second marker ring, and a third marker ring.

4. The method of claim 3, wherein the distance between the first marker ring and the second marker ring is the same as the distance between the second marker ring and the third marker ring.

5. The method of claim 1, wherein the plurality of marker rings are marked on a sleeve that is fitted to the surface of the tool.

6. The method of claim 1, further including determining the orientation of the cutting portion by assessing the effect of parallax on the observed spacing between the rotating plurality of marker rings.

7. A method of cutting for use in surgery, comprising:
   operating a drive unit so as to rotate a cutting tool about a tool axis, the cutting tool being fitted into the drive unit and having an elongate shaft which extends from the drive unit, the elongate shaft having (i) cutting teeth configured to cut during rotation thereof, and (ii) a plurality of marker rings positioned between the cutting teeth and the drive unit, the plurality of marker rings arranged in a predetermined pattern and extending at least partially around the tool axis;
   using at least two spaced apart receiving devices while the cutting tool is rotating about the tool axis so as to identify a respective apparent outline for each of the rotating plurality of marker rings as detected by the receiving devices; and
   generating information as to position and orientation of the cutting tool relative to the receiving devices by analyzing the respective apparent outlines.

8. The method of claim 7, wherein the plurality of marker rings are more reflective than the surface of the shaft on which they are arranged.

9. The method of claim 7, wherein each of the plurality of marker rings is spaced apart from the drive unit.

10. The method of claim 7, wherein planes defined by axially spaced edges of each of the plurality of rings are parallel to one another and perpendicular to the tool axis.

11. The method of claim 7, wherein the plurality of rings is marked on a sleeve that is fitted to the surface of the tool.

12. The method of claim 7, further comprising:
defining, based on the apparent outline of at least one of the plurality of marker rings, the axis of the shaft, the axis of the shaft extending generally along a line which is equidistant from opposite edges of the apparent outline of the at least one of the plurality of marker rings, and
defining, based on the apparent outline, the center line of each of the plurality of marker rings which intersect the axis of the shaft at a point which is equidistant from the opposite edges, extending perpendicular to the shaft axis, of the plurality of marker rings.

13. The method of claim 7, further including determining orientation of the cutting tool by assessing the effect of parallax on the observed spacing between the plurality of marker rings.

14. The method of claim 1, further comprising:
identifying the tool using the plurality of marker rings.

15. The method of claim 7, further comprising:
identifying the tool using the plurality of marker rings.

* * * * *